United States Patent
Kumar et al.

(10) Patent No.: US 9,676,707 B2
(45) Date of Patent: Jun. 13, 2017

(54) PROCESS FOR THE SYNTHESIS OF [6,6]-PHENYL-$C_{61}$ BUTYRIC ACID PENTYL ESTER (PC61BP)

(71) Applicant: Council of Scientific & Industrial Research, New Delhi (IN)

(72) Inventors: Rachana Kumar, New Delhi (IN); Samya Naqvi, New Delhi (IN); Neha Gupta, New Delhi (IN); Suresh Chand, New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/047,342

(22) Filed: Feb. 18, 2016

(65) Prior Publication Data

US 2016/0237018 A1  Aug. 18, 2016

(30) Foreign Application Priority Data

Feb. 18, 2015  (IN) .............................. 458/DEL/2015

(51) Int. Cl.
| | | |
|---|---|---|
| C07C 245/18 | (2006.01) | |
| C07C 303/40 | (2006.01) | |
| C07C 303/44 | (2006.01) | |
| C07C 313/06 | (2006.01) | |
| C07C 67/333 | (2006.01) | |
| C07C 67/343 | (2006.01) | |

(52) U.S. Cl.
CPC .......... *C07C 303/44* (2013.01); *C07C 67/333* (2013.01); *C07C 67/343* (2013.01); *C07C 245/18* (2013.01); *C07C 303/40* (2013.01); *C07C 313/06* (2013.01); *C07C 2104/00* (2013.01)

(58) Field of Classification Search
CPC ... C07C 245/18; C07C 303/40; C07C 303/44; C07C 313/06; C07C 67/333; C07C 67/343; C07C 2104/00
See application file for complete search history.

(56) References Cited

U.S. PATENT DOCUMENTS

2014/0066647 A1  3/2014  Ng et al.

OTHER PUBLICATIONS

Zheng et al., "Methanofullerenes Used as Electron Acceptors in Polymer Photovoltaic Devices," J. Phys. Chem. B., 2004, 108(32) 11921.*
Shen et al., Macromolecules 2013, 46, pp. 9575-9586, "Enhancing Photovoltaic Performance of Copolymers Containing Thiophene Unit with D-A Conjugated Side Chain by Rational Molecular Design".
You et al., Nature Communications 2013, 4:1446, p. 1-10, "A polymer tandem solar cell with 10.6% power conversion efficiency".
Scharber et al., Advanced Materials 2006, 18, pp. 789-794, "Design Rules for Donors in Bulk-Heterojunction Solar Cells—Towards 10% Energy-Conversion Efficiency".
Hummelen et at., The Journal of Organic Chemistry 1995, 60, pp. 532-538, "Preparation and Characterization of Fulleroid and Methanofullerene Derivatives".
Lenes et al., Advanced Materials, 2008, 20, pp. 2116-2119, "Fullerene Bisadducts for Enhanced Open-Circuit Voltages and Efficiencies in Polymer Solar Cells".
Burke et al., 2013, 6, pp. 2053-2066, Energy & Environmental Science, "Green chemistry for organic solar cells".
Tuktarov et al., Tetrahedron Letters 54, Apr. 2013, pp. 2146-2148, "Catalytic Cycloaddition of Diazo Amides to Fullerene $C_{60}$".
Kumar et al., RSC Advances, 2014, 4, pp. 15675-15677, "A cost effective and eco-friendly one-pot process for PC61BM synthesis under aerobic conditions".

* cited by examiner

*Primary Examiner* — Paul A Zucker
*Assistant Examiner* — Mark Luderer
(74) *Attorney, Agent, or Firm* — Knobbe, Martens, Olson & Bear, LLP

(57) ABSTRACT

A total green, eco-friendly process for the synthesis of new acceptor molecule [6,6]-phenyl-$C_{61}$-butyric acid pentyl ester (PC61BP) in high yields is carried under aerobic conditions showing better performance as acceptor in organic solar cells. More importantly this process causes the low cost synthesis of PC61BP in good yield without involving harmful and costly catalysts or chemicals.

7 Claims, 4 Drawing Sheets

PROCESS FOR THE SYNTHESIS OF [6,6]-PHENYL-$C_{61}$BUTYRIC ACID PENTYL ESTER (PC61BP)

FIELD OF THE INVENTION

The present invention relates to total green, eco-friendly process for the synthesis of new acceptor molecule [6,6]-phenyl-$C_{61}$-butyric acid pentyl ester (PC61BP) in high yields. More particularly, the present invention relates to a process for the preparation of PC61BP under aerobic conditions (in air) which is showing better performance as acceptor in organic solar cells compared to conventional material [6,6]-phenyl-$C_{61}$-butyric acid methyl ester (PC61BM). More importantly this process causes the low cost synthesis of PC61BP in good yield without involving harmful and costly catalysts or chemicals.

BACKGROUND OF THE INVENTION

Organic solar cells contribute immensely towards the renewable source of energy generation at low cost and research in this area is increasing exponentially every year (Shen et al., Macromolecules 2013, 46, 9575-9586). Organic solar cells are regarded as potentially environment cordial source of power compared to other methods of energy production. Organic solar cells comprise of heterostructure of two semiconductor components with different and compatible energy levels. Bulk heterojunction is the most conventional geometry where the active layer comprises of donor and acceptor molecules sandwiched between a low workfunction and high workfunction electrodes which collect electrons and holes respectively. So far the intensive research efforts have produced the solar cells with efficiency as high as 10.6% (You et al., Nature Comm. 2012, 4:1446, 1-10). The most commonly used fullerene based acceptor material is [6,6]-Phenyl-$C_{61}$-butyric acid methyl ester (PC61BM) particularly for polymer based organic solar cells and transistors (Scharber et al., Adv. Mater. 2006, 18, 789). Reported methods of PC61BM synthesis involves the dipolar cycloaddition reaction of diazoalkane which are generated insitu via base induced decomposition of tosylhydrazone derivative with 35% yield as the highest (Hummelen et at., J. Org. Chem. 1995, 60, 532; Lenes et al., Adv. Mater. 2008, 20, 2116) using pyridine and sodium methoxide under inert atmosphere for diazomethane generation. US patent number 2014/0066647 discloses the highest possible yield for PC61BM to be 40% on optimizing the fullerene, hydrazone and sodium methoxide ratios in pyridine. However, the most needful aspect of their application on large scale has been neglected which is, the impact on environment due to disposals during material synthesis (Daniel et al., Energy Environ. Sci., 2013, 6, 2053). A general catalytic procedure for the cycloaddition of diazo amides to fullerene[60] in the presence of the three-component catalyst, Pd(acac)$_2$-PPh$_3$-Et$_3$Al, was reported by Tuktarov et al., (Tetrahedron Lett. 2013, 54, 2146) where, depending on the reaction conditions, pyrazolinofullerenes or methanofullerenes were formed. The inventors have previously reported the synthesis of PC61BM (RSC Adv. 2014, 4, 15675) in presence of triethyl amine as catalyst in dichloromethane under air in ~40% yield. The limitations with the process were, low yield and use of chlorinated solvents. An eco-friendly and cost-effective methodology with high yield is essentially required to mitigate the environmental externalities of manufacturing on large scale for such materials. Also, there is a need of alternate material with better performance and should also mimic the structure of PC61BM to retain its inherent electrical and film properties. In this regard, we have come up with a process of synthesis of new fullerene derivative, i.e., [6,6]-phenyl-$C_{61}$-butyric acid pentyl ester (PC61BP) under the present invention using different types of amines (secondary and tertiary) in ethyl acetate as well as in dichloromethane for better yields and properties in organic solar cells.

OBJECTIVES OF THE INVENTION

The main object of the present invention is to provide a process for the synthesis of new acceptor molecule [6,6]-phenyl-$C_{61}$-butyric acid pentyl ester (PC61BP).

Another object of the present invention is to provide a process for the preparation of a PC61BP under in air.

Yet another object of the present invention is to provide a process wherein amine like, diethyl amine or di-isopropyl amine or triethyl amine is used as catalyst.

Yet another object of the present invention is to provide a process wherein ethyl acetate or dichloromethane is used as solvent.

Yet another object of the present invention is to avoid harmful chemicals like pyridine.

Yet another object of the present invention is to avoid hygroscopic materials like sodium methoxide.

Yet another object of the present invention is to provide PC61BP synthesis process in good yield for solar cells and other possible applications.

SUMMARY OF THE INVENTION

Present invention provides a process for the synthesis of [6,6]-phenyl($C_{61}$)butyric acid pentyl ester (PC61BP) (FIG. 1, Formula I) from hydrazone precursor (pentyl-4-benzoyl-butyrate p-tosylhydrazone) (FIG. 3, Formula II) in presence of mild base catalyst (diethyl amine or diisopropyl amine or triethyl amine) and the temperature −10° C. or 0° C. or 10° C. in air to obtain [5,6]-phenyl($C_{61}$)butyric acid pentyl ester (FIG. 5, Formula III) which on further refluxing yields [6,6]-phenyl($C_{61}$)butyric acid pentyl ester in high yield of 55% (FIG. 1, Formula I).

Accordingly, present invention provides a process for the synthesis of [6,6]-phenyl($C_{61}$)butyric acid pentyl ester (PC61BP) of general Formula 1, comprising the steps of:

(i) reacting organic acid ester and p-toluene sulphonyl hydrazide in the range of 1:1.2 to 1:1.5 by dissolving the compounds in methanol and refluxing with stirring for 4-6 hrs followed by stirring at room temperature in the range of 20-30° C. for a period in the range of 10-12 hr and cooling at 0-10° C. to obtain organic acid ester hydrazone crystals;

(ii) washing the hydrazone crystals as obtained in step (i) with cold methanol to obtain pure organic acid ester hydrazone;

(iii) dissolving organic acid ester hydrazone as obtained in step (ii) in organic solvent and cooled to −10 to 10° C., followed by adding alkyl amine and stirring for a period in the range of 1-3 hrs to obtain organic acid ester hydrazone solution;

(iv) adding fullerene solution to organic acid ester hydrazone solution as obtained in step (iii) in the ratio ranging between 1:0.33-1:0.5 and temperature raised to 80-100° C. by continuous stirring for a period in the range of 18-24 hrs followed by precipitating with methanol to obtain a mixture;

(v) centrifugating the mixture as obtained from step (iv) to obtain a solid;
(vi) loading the solid as obtained in step (v) on silica gel column and purifying it with toluene to obtain unreacted fullerene and monoadduct [5,6]PC61BP;
(vii) refluxing the monoadduct as obtained in step (vi) in o-dichlorobenzene for a period in the range of 5-7 hrs followed by centrifuging to obtain [6,6]-phenyl($C_{61}$) butyric acid pentyl ester.

In an embodiment of the present invention, the organic acid ester is preferably pentyl-4-benzoylbutyrate and organic acid ester hydrazone is preferably pentyl-4-benzoylbutyrate p-tosylhydrazone.

In another embodiment of the present invention, the organic solvent used to dissolve organic acid ester hydrazone is selected from dichloromethane or ethyl acetate and the alkyl amine used to convert said organic acid ester hydrazone to diazo-intermediate (diazomethane) is either a secondary or tertiary amine selected from diethyl amine, diisopropyl amine and triethyl amine.

In yet another embodiment of the present invention, 3.36 mg/mL fullerene solution is prepared using organic solvent selected from o-dichlorobenzene or toluene.

DETAILED DESCRIPTION OF THE INVENTION

According to the present invention, methanofullerene, [6,6]-phenyl-$C_{61}$-butyric acid pentyl ester (PC61BP) is synthesized in high yields in ethyl acetate or dichloromethane in presence of secondary or tertiary amine under air at temperature −10 to 10° C.

Figure 9:
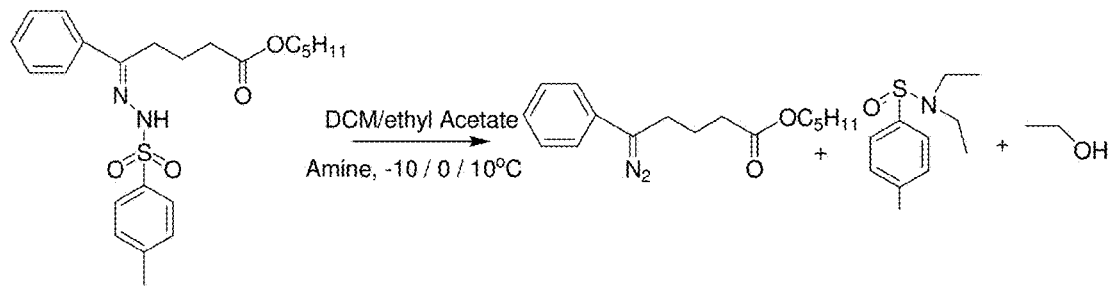
FIG. 9. Mechanism of diazomethane formation.
Figure 10:
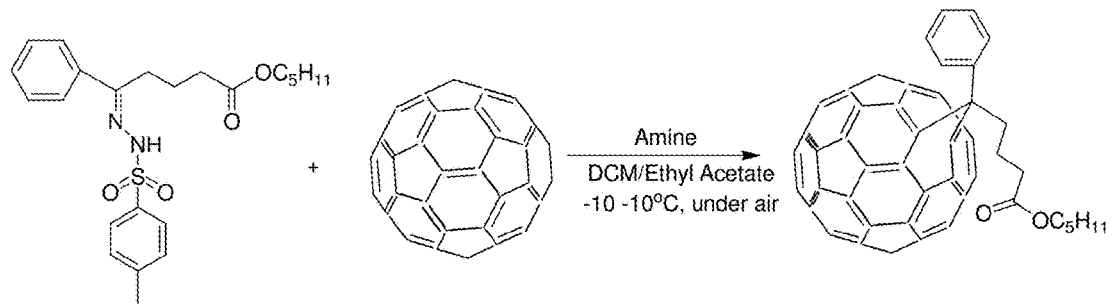
FIG. 10. Synthesis of [5,6]-phenyl-$C_{61}$-butyric acid pentyl ester.
Figure 11:
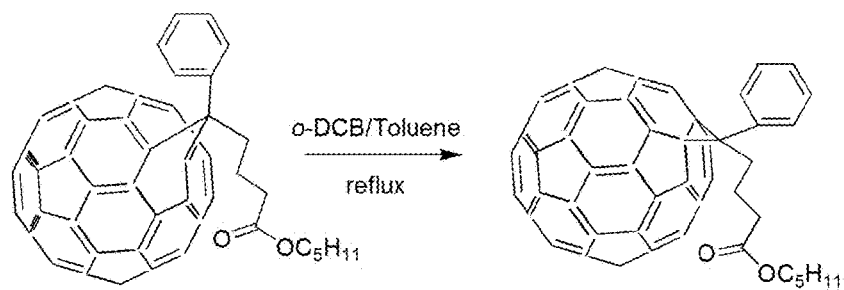
FIG. 11. Synthesis of [6,6]-phenyl-$C_{61}$-butyric acid pentyl ester.

The process of invention involves, (i) synthesis of ester hydrazone (1b) from its ester by (1a) refluxing in methanol with p-toluenesulfonyl hydrazide for 24 hours, (ii) insitu preparation of diazomethane (1c) from its hydrazone (1b) in presence of mild base (secondary or tertiary amine) in dichloromethane or ethyl acetate at −10° C. or 0° C. or 10° C. in air (FIG. 9, FIG. 10), (iii) cycloaddition of thus prepared diazomethane on fullerene by addition of o-dichlorobenzene solution of fullerene and heated at 80 to 100° C. for 18-24 hour (FIG. 10), (iv) alternatively a toluene solution of fullerene [60] is added and heated at 80 to 100° C. for 18-24 hour, (v) thus prepared [5,6]PC61BP is purified by column chromatography using silica gel as stationary phase and toluene as eluent, (vi) [5,6] isomer is converted to [6,6] isomer by refluxing in o-dichlorobenzene for 5-7 hour, precipitated with methanol and collected by centrifugation (FIG. 11), (vii) alternatively [5,6] isomer is re-dissolved in toluene and refluxed for 5-7 hour to convert into [6,6] isomer, (viii) highest yield of 55% is achieved with diethyl amine as catalyst.

The novelty of the invention is the synthesis of [6,6]-phenyl-$C_{61}$-butyric acid pentyl ester (PC61BP) under total aerobic condition (in air) without use of any metallic catalyst or harmful chemicals with high yields. The innovative step involves the synthesis of diazomethane intermediate. In this inventive step, hydrazone precursor is dissolved in ethyl acetate or dichloromethane at −10° C. or 0° C. or 10° C. and secondary amine (diethyl amine or diisopropyl amine) or tertiary amine (triethyl amine) is added as mild catalyst converting hydrazone into diazomethane.

Figure 1:
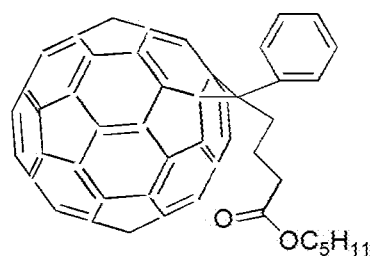
FIG. 1. Chemical structure of [6,6] PC61BP with Formula I.
Figure 2:
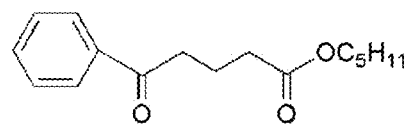
FIG. 2. Chemical structure of butyric acid ester (1a).
Figure 3:
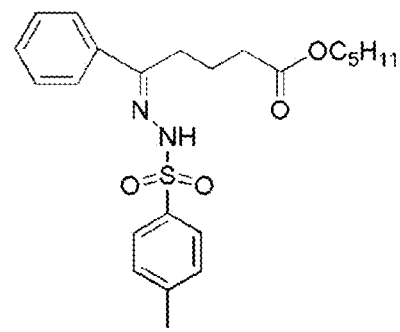
FIG. 3. Chemical structure of butyric acid ester hydrazone (1b) with Formula II.
Figure 4:
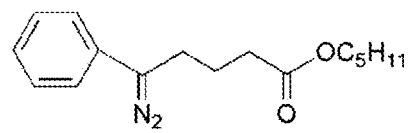
FIG. 4. Chemical structure of diazomethane intermediate (1c).
Figure 5:
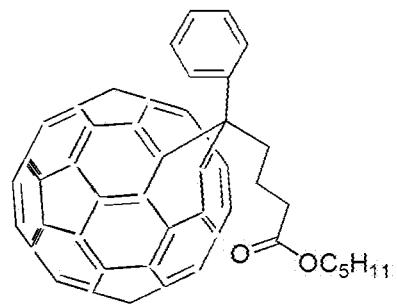
FIG. 5. Chemical structure of [5,6]PC61BP with Formula III.
Figure 6:
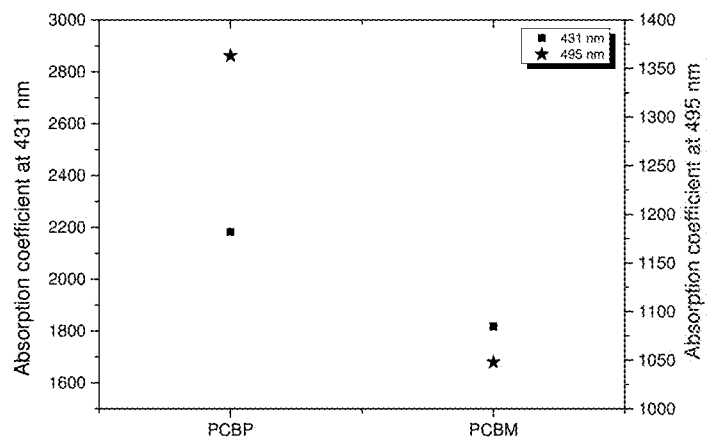
FIG. 6. Comparative Absorption coefficient ($M^{-1}$ $cm^{-1}$) graph of PC61BP and PC61BM at two different absorption wavelengths.
Figure 7:
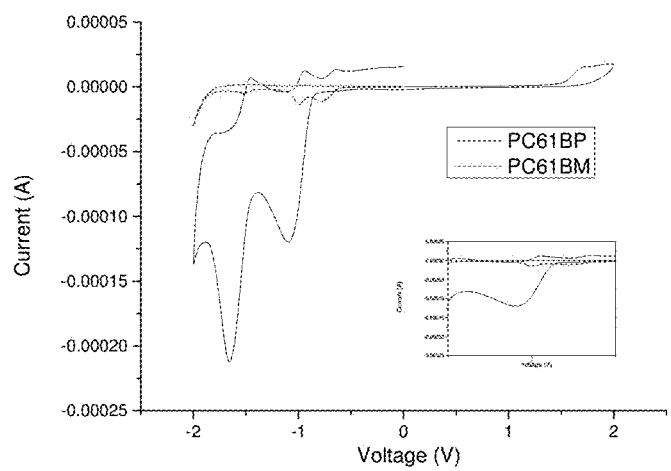
FIG. 7. Comparative cyclic voltammogram of PC61BP and PC61BM under same conditions. PCBP shows onset reduction potential higher than PCBM.
Figure 8:
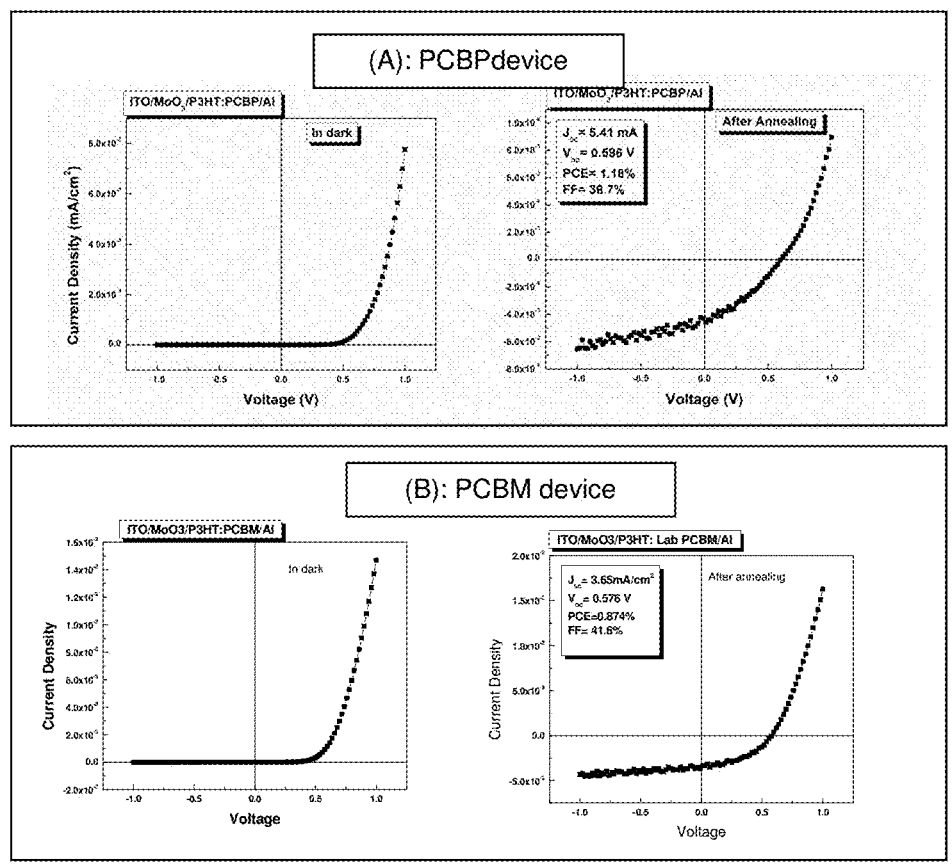
FIG. 8. Device characteristics of PC61BP(A) and PC61BM (B) under same conditions and geometry fabricated in air.

Novelty in the present invention also lies in the synthesis of new diazo-intermediate (1-Phenyl-1-(3-(pentyloxycarbonyl)propyl)diazomethane) than in the prior art (RSC ADV.2014,4,15675) in presence of amine catalyst (secondary or tertiary amine) in dichloromethane as well as in ethyl acetate as solvent in air for the synthesis of new product PC61BP. Where as in the prior art, synthesis of different diazo intermediate is reported in dichloromethane with triethyl amine only. The beauty of the invention is the generation of new diazo intermediate from precursor hydrazone in presence of different types of amines and solvent to ultimately get the best possible yield of PC61BP. Further, fullerene solution (o-dichlorobenzene/toluene) is added to diazomethane solution resulting in [5,6] isomer of phenyl-$C_{61}$-butyric acid pentyl ester which is isolated and purified by column chromatography using toluene as eluent. This [5,6] isomer is converted quantitatively into [6,6] isomer by refluxing in o-dichlorobenzene/toluene. Thus prepared [6,6]-phenyl-$C_{61}$-butyric acid pentyl ester in highest yield in presence of diethyl amine (55%), finds its applications as better performing acceptor material in organic photovoltaic solar cells in place of PC61BM. PC61BP shows higher absorption coefficient ($M^{-1}$ $cm^{-1}$) than PC61BM under same conditions (FIG. 6). Another advantage of the present material PC61BP is it shows 260 mV cathodic shifted in reduction potential compared to PC61BM as cathodic shift of reduction potential (FIG. 7) uplifts the LUMO level of acceptor material which directly improves the power conversion efficiency of organic solar cells. Power conversion efficiency (PCE) improvement by 35% is obtained with PC61BP compared to PC61BM for same device geometry fabricated in air as shown in FIG. 8.

The inventive steps involved in the present invention are
i) Synthesis of new diazo-intermediate (1-Phenyl-1-(3-(pentyloxycarbonyl)propyl)diazomethane) in presence of mild base catalyst which is either a secondary or tertiary amine in air in ethyl acetate or dichloromethane solvent yielding PC61BP in high yields.
ii) Mild base catalyst is diethyl amine or diisopropyl amine or triethyl amine.
iii) Highest yield (55%) of PC61BP is obtained with diethyl amine.
iv) This process is envisaged as a green chemistry and will open channels for the large scale synthesis of PC61BP for solar cells applications without bothering for controlled environment conditions.

EXAMPLES

The following examples are given by way of illustration of the present invention and therefore should not be construed to limit the scope of the present invention.

Example 1

Pentyl4-benzoylbutyrate (1.364 g, 5.2 mM) and p-toluene sulfonyl hydrazide (1.2 eq, 1.162-g, 6.24 mM) are dissolved in methanol (50 mL) and refluxed with stirring for 6 hr followed by stirring at room temperature (25° C.) for over night (12 hr). Crystals of hydrazone come out on cooling and collected after washing with cold methanol. Pentyl-4-benzoylbutyrate p-tosylhydrazone (60.27 mg, 0.14 mM) is dissolved in ethyl acetate (10 mL) and cooled down to −10° C. Catalytic amount of diethyl amine (0.7 mL) is added and stirred for three hours at this temperature. A solution of $C_{60}$ (0.3 eq, 33.6 mg, 0.046 mM) in o-dichlorobenzene (10 mL) is added and temperature is raised to 80° C. Stirred at this temperature for 18 hour followed by precipitation with methanol. Solid is collected by cerifugation and loaded on silica gel column (200 mm×18 mm) for purification with toluene. Unreacted fullerene comes as first fraction followed by monoadduct ([5,6]PC61BP, 55% yield). [5,6]PC61BP is converted in to [6,6] isomer by refluxing in o-dichlorobenzene (5 mg/mL) for 5 hour (yield 100%). $^1H$ NMR (δ, $CDCl_3$): 7.80 (d, 2H, o-H Ph), 7.48 (t, 2H, m-H Ph), 7.40 (m, 1H, p-H Ph), 4.0 (t, 2H, OCH2), 2.84 (m, 4H, PhCCH2, COOCH2CH2), 2.45 (t, 2H, CH2COOR), 2.11 (q, 2H, CH2CH2COOR), 1.53 (m, 2H, COOCH2CH2CH2), 1.18 (m, 2H, COOCH2CH2CH2CH2), 0.80 (t, 3H, COOCH2CH2CH2CH3). $^{13}C$ NMR (δ, $CDCl_3$): 172.5 (CO2Me), 32 peaks between 150-127, 78.8, 63.7, 50.7, 33.1, 32.7, 30.9, 28.6, 27.0, 21.3, 12.9 ppm. UV-vis ($\lambda_{max}$, nm)=404, 430, 493 and 697.

Example 2

Pentyl-4-benzoylbutyrate p-tosylhydrazone (60.27 mg, 0.14 mM) is dissolved in ethyl acetate (10 mL) and cooled down to 0° C. Catalytic amount of diethyl amine (1 mL) is added and stirred for three hours at this temperature. A solution of $C_{60}$ (0.3 eq, 33.6 mg, 0.046 mM) in o-dichlorobenzene (10 mL) is added and temperature is raised to 90° C. Stirred at this temperature for 24 hour followed by precipitation with methanol. Solid is collected by cerifugation and loaded on silica gel column (200 mm×18 mm) for purification with toluene. Unreacted fullerene comes as first fraction followed by monoadduct ([5,6]PC61BP, 55% yield). [5,6]PC61BP is converted in to [6,6] isomer by refluxing in o-dichlorobenzene (5 mg/mL) for 5-7 hour (yield 100%).

Example 3

Pentyl-4-benzoylbutyrate p-tosylhydrazone (60.27 mg, 0.14 mM) is dissolved in ethyl acetate (10 mL) and cooled down to 10° C. Catalytic amount of diethyl amine (0.5 mL) is added and stirred for one hour at this temperature. A solution of $C_{60}$ (0.5 eq, 50.4 mg, 0.07 mM) in o-dichlorobenzene (10 mL) is added and temperature is raised to 100° C. Stirred at this temperature for 24 hour followed by precipitation with methanol. Solid is collected by cerifugation and loaded on silica gel column (200 mm×18 mm) for purification with toluene. Unreacted fullerene comes as first fraction followed by monoadduct ([5,6]PC61BP, 55% yield). [5,6]PC61BP is converted in to [6,6] isomer by refluxing in o-dichlorobenzene (5 mg/mL) for 5-7 hour (yield 100%).

Example 4

Pentyl-4-benzoylbutyrate p-tosylhydrazone (60.27 mg, 0.14 mM) is dissolved in ethyl acetate (10 mL) and cooled down to −10° C. Catalytic amount of diethyl amine (0.7 mL) is added and stirred for three hours at this temperature. A solution of $C_{60}$ (0.3 eq, 33.6 mg, 0.046 mM) in o-dichlorobenzene (10 mL) is added and temperature is raised to 80 to 100° C. Stirred at this temperature for 18 hour followed by precipitation with methanol. Solid is collected by cerifugation and loaded on silica gel column (200 mm×18 mm) for purification with touene. Unreacted fullerene comes as first fraction followed by monoadduct ([5,6]PC61BP, 55% yield). [5,6]PC61BP is converted in to [6,6] isomer by refluxing in o-dichlorobenzene (5 mg/mL) for 5-7 hour (yield 100%).

Example 5

Pentyl4-benzoylbutyrate p-tosylhydrazone (60.27 mg, 0.14 mM) is dissolved in dichloromethane (10 mL) and cooled down to 0° C. Catalytic amount of diethyl amine (0.7 mL) is added and stirred for three hours at this temperature. A solution of $C_{60}$ (0.3 eq, 33.6 mg, 0.046 mM) in o-dichlorobenzene (10 mL) is added and temperature is raised to 90° C. Stirred at this temperature for 20 hour followed by precipitation with methanol. Solid is collected by cerifugation and loaded on silica gel column (200 mm×18 mm) for purification with toluene. Unreacted fullerene comes as first fraction followed by monoadduct ([5,6]PC61BP, 50% yield). [5,6]PC61BP is converted in to [6,6] isomer by refluxing in o-dichlorobenzene (5 mg/mL) for 7 hour (yield 100%).

Example 6

Pentyl-4-benzoylbutyrate p-tosylhydrazone (60.27 mg, 0.14 mM) is dissolved in dichloromethane (10 mL) and cooled down to 0° C. Catalytic amount of diisopropyl amine (0.8 mL) is added and stirred for three hours at this temperature. A solution of $C_{60}$ (0.3 eq, 33.6 mg, 0.046 mM) in o-dichlorobenzene (10 mL) is added and temperature is raised to 80° C. Stirred at this temperature for 18 hour followed by precipitation with methanol. Solid is collected by cerifugation and loaded on silica gel column (200 mm×18 mm) for purification with toluene. Unreacted fullerene comes as first fraction followed by monoadduct ([5,6]PC61BP, 35% yield). [5,6]PC61BP is converted in to [6,6] isomer by refluxing in o-dichlorobenzene (5 mg/mL) for 6 hour (yield 100%).

Example 7

Pentyl-4-benzoylbutyrate p-tosylhydrazone (60.27 mg, 0.14 mM) is dissolved in dichloromethane (12 mL) and cooled down to 0° C. Catalytic amount of triethylamine (0.7 mL) is added and stirred for 1 hour at this temperature. A solution of $C_{60}$ (0.5 eq, 50.4 mg, 0.07 mM) in o-dichlorobenzene (12 mL) is added and temperature is raised to 100° C. Stirred at this temperature for 22 hour followed by precipitation with methanol. Solid is collected by cerifugation and loaded on silica gel column (200 mm×18 mm or) for purification with toluene. Unreacted fullerene comes as first fraction followed by monoadduct ([5,6]PC61BP, 40% yield). [5,6]PC61BP is converted in to [6,6] isomer by refluxing in o-dichlorobenzene (5 mg/mL) for 5 hour (yield 100%).

Example 8

Pentyl-4-benzoylbutyrate p-tosylhydrazone (60.27 mg, 0.14 mM) is dissolved in dichloromethane (10 mL) and cooled down to 10° C. Catalytic amount of triethylamine (0.6 mL) is added and stirred for 3 hours at this temperature. A solution of $C_{60}$ (0.5 eq, 50.4 mg, 0.07 mM) in toluene (12 mL) is added and temperature is raised to 90° C. Stirred at this temperature for 20 hour followed by precipitation with methanol. Solid is collected by centrifugation and loaded on silica gel column (200 mm×18 mm) for purification with toluene. Unreacted fullerene comes as first fraction followed by monoadduct ([5,6]PC61BP, 40% yield). [5,6]PC61BP is converted in to [6,6] isomer by refluxing in toluene (5 mg/mL) for 5 hour (yield 100%).

ADVANTAGES OF THE INVENTION

1) One pot process for the synthesis of [6,6]PC61BP in air
2) Cost effective and eco-friendly process as harmful chemicals like, pyridine are completely avoided
3) Doesn't use hygroscopic chemicals like sodium methoxide
4) Catalysts (base) are eco-friendly
5) Avoids completely the use of inert atmosphere in any step of synthesis making the process very cost effective.
6) High yield and better properties of PC61BP compared to prior art.

We claim:

1. A process for the synthesis of [6,6]-phenyl($C_{61}$)butyric acid pentyl ester (PC61BP) of Formula 1, comprising the steps of:

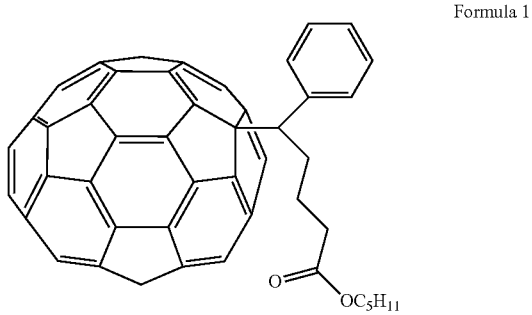

Formula 1 i) reacting an organic acid ester and a p-toluene sulphonyl hydrazide in the range of 1:1.2 to 1:1.5 by dissolving the compounds in methanol and refluxing with stirring for 4-6 hrs followed by stirring at room temperature in the range of 20-30° C. for a period in the range of 10-12 hr and cooling at 0-10° C. to obtain organic acid ester hydrazone crystals;
ii) washing the hydrazone crystals as obtained in step (i) with cold methanol to obtain pure organic acid ester hydrazone;
iii) dissolving the organic acid ester hydrazone as obtained in step (ii) in an organic solvent and cooled to −10 to 10° C., followed by adding alkyl amine and stirring for a period in the range of 1-3 hrs to obtain an organic acid ester hydrazone solution;
iv) adding a fullerene solution to the organic acid ester hydrazone solution as obtained in step (iii) in the ratio ranging between 1:0.33-1:0.5 and temperature raised to 80-100° C. by continuous stirring for a period in the range of 18-24 hrs followed by precipitating with methanol to obtain a mixture;
v) centrifuging the mixture as obtained from step (iv) to obtain a solid;
vi) loading the solid as obtained in step (v) on a silica gel column and purifying it with toluene to obtain unreacted fullerene and monoadduct [5,6]PC61BP;
vii) refluxing the monoadduct as obtained in step (vi) in o-dichlorobenzene for a period in the range of 5-7 hrs followed by centrifuging to obtain [6,6]-phenyl($C_{61}$) butyric acid pentyl ester.

2. The process as claimed in claim 1, wherein the organic acid ester is pentyl-4-benzoylbutyrate.

3. The process as claimed in claim 1, wherein the organic acid ester hydrazone is pentyl-4-benzoylbutyrate p-tosylhydrazone.

4. The process as claimed in step (iii) of claim 1, wherein the organic solvent used is ethyl acetate or dichloromethane.

5. The process as claimed in claim 1, wherein diazomethane is generated insitu by using the organic acid ester hydrazone in the presence of triethylamine as base.

6. The process as claimed in claim 1, wherein the alkyl amine used is selected from the group consisting of diethyl amine and diisopropyl amine.

7. The process as claimed in step (iv) of claim 1, wherein fullerene solution is prepared using an organic solvent selected from the group consisting of o-dichlorobenzene and toluene.

* * * * *